United States Patent [19]

Poole

[11] Patent Number: 5,760,279
[45] Date of Patent: Jun. 2, 1998

[54] PROCESS FOR THE CARBONYLATION OF ALKYL ALCOHOLS

[75] Inventor: Andrew David Poole, North Humberside, United Kingdom

[73] Assignee: BP Chemicals Limited, London, England

[21] Appl. No.: 661,950

[22] Filed: Jun. 12, 1996

[30] Foreign Application Priority Data

Jun. 19, 1995 [GB] United Kingdom ............. 9512427

[51] Int. Cl.$^6$ ............................. C07C 67/36; C07C 51/12
[52] U.S. Cl. ......................... 560/232; 562/519; 562/520; 562/517
[58] Field of Search ..................... 562/519, 520, 562/517; 560/232

[56] References Cited

U.S. PATENT DOCUMENTS

| | | | |
|---|---|---|---|
| 3,769,329 | 10/1973 | Paulik et al. | 260/488 V |
| 4,994,608 | 2/1991 | Torrence et al. | 562/519 |
| 5,001,259 | 3/1991 | Smith et al. | 562/519 |
| 5,214,203 | 5/1993 | Koyama et al. | 562/519 |

FOREIGN PATENT DOCUMENTS

| | | |
|---|---|---|
| 1258469 | 8/1989 | Canada . |
| 055618 | 7/1982 | European Pat. Off. . |
| 0 573 189 | 12/1993 | European Pat. Off. . |
| 573189 | 12/1993 | European Pat. Off. . |
| 48-049713 | 10/1973 | Japan . |
| 48-94277 | 4/1975 | Japan . |
| 50-047921 | 4/1975 | Japan . |
| 2063265 | 6/1961 | United Kingdom . |
| 2 146 637 | 4/1985 | United Kingdom . |
| 2146637 | 4/1985 | United Kingdom . |

OTHER PUBLICATIONS

"The Rhodium–Catalyzed Methanol Carbonylation to Acetic Acid at Low Water Concentrations: The Effect of Iodide and Acetate on Catalyst Activity and Stability"; *Journal of Molecular Catalysts*; B. L. Smith et al.; vol. 39, pp. 115–136; ©1987.

"Photo–, Electro–, and Thermal Carbonylation of Alkyl Iodides in the Presence of Group 7 and 8–10 Metal Carbonyl Catalysts"; *Journal of Organometallic Chemistry*; T. Kondo et al.; vol. 473, pp. 163–173; ©1994.

"Activity of the Catalyst RhNaX, Promoted by Some Transition Metal Oxides, in the Carbonylation of Methanol with Carbon Monoxide at Atmospheric Pressure"; *Aliphatics*; B. K. Nefedov et al.; vol. 90, pp. 555; ©1979.

*Primary Examiner*—Paul J. Killos
*Assistant Examiner*—Rosalynd Keys
*Attorney, Agent, or Firm*—Fay, Sharpe, Beall, Fagan, Minnich & McKee

[57] ABSTRACT

The use of manganese at a molar ratio of manganese:rhodium of (0.2 to 20):1 to stabilize the rhodium catalyst during the rhodium catalyzed carbonylation of alkyl alcohols and/or recovery of carbonylation product therefrom at low partial pressure of carbon monoxide of less than or equal to 7 bar.

23 Claims, No Drawings

PROCESS FOR THE CARBONYLATION OF ALKYL ALCOHOLS

The present invention relates to a process for the carbonylation of alkyl alcohols and/or reactive derivatives thereof in the presence of a rhodium catalyst.

Carbonylation processes in the presence of rhodium catalysts are known and are described, for example, in U.S. Pat. No. 3,769,329 and EP-0055618-A.

J. Molecular Catalysis, 39 (1987) 115–136 relates to addition of iodide salts to rhodium catalyst solutions for methanol carbonylation at low water concentrations (<2M) to promote the rate of carbonylation and stabilize the rhodium catalyst. The rate of methanol carbonylation in the presence of $MnI_2$ was reported together with the rates for a large number of other iodide salts at a total reaction pressure of 400 psig. We believe that under such conditions, the rate of the carbonylation reaction is not limited by the partial pressure of carbon monoxide. Furthermore, the molar ratio of manganese:rhodium in the reported experiment using manganese is very high and is estimated to be (>90):1.

Operation of carbonylation processes at low partial pressure of carbon monoxide is desirable because it leads to an increased utilization of the carbon monoxide reactant, for example, by reducing loss of carbon monoxide in the gases vented from the reactor.

A problem with rhodium-catalyzed carbonylation reactions is that at low partial pressure of carbon monoxide in the carbonylation reactor, that is at less than or equal to 7 bar, the rate of the carbonylation may be limited by the partial pressure of carbon monoxide.

The technical problem to be solved is to provide a process for the carbonylation of an alkyl alcohol and /or a reactive derivative thereof in the presence of a rhodium catalyst and an alkyl halide which overcomes this problem.

Thus, according to the present invention there is provided a process for the carbonylation of an alkyl alcohol and/or a reactive derivative thereof which process comprises the steps of (i) contacting, in a carbonylation reactor, said alcohol and/or a reactive derivative thereof with carbon monoxide in a liquid reaction composition comprising (a) a rhodium catalyst, (b) alkyl halide, and (c) at least a finite concentration of water and (ii) recovering carbonylation product from said liquid reaction composition characterized in that there is present in the carbonylation and/or product recovery steps a partial pressure of carbon monoxide less than or equal to 7 bar and a stabiliser for the rhodium catalyst comprising manganese, at a molar ratio of manganese:rhodium of (0.2 to 20):1.

In the process of the present invention the use of a manganese stabilizer for the rhodium catalyst has a beneficial effect on the rate of rhodium-catalyzed carbonylation of an alkyl alcohol and/or a reactive derivative thereof at a partial pressure of carbon monoxide of less than or equal to 7 bar partial pressure, which would be carbonylation rate limiting in the absence of the manganese stabilizer.

Thus according to one aspect of the present invention there is provided a process for the carbonylation of an alkyl alcohol and/or a reactive derivative thereof which process comprises contacting, in a carbonylation reactor, an alcohol and/or a reactive derivative thereof with carbon monoxide in a liquid reaction composition at a partial pressure of carbon monoxide in said reactor of less than or equal to 7 bar, in which the liquid reaction composition comprises (a) a rhodium catalyst, (b) alkyl halide, (c) at least a finite concentration of water and (d) a stabiliser for the rhodium catalyst comprising manganese in a form active for promotion of the carbonylation reaction at a molar ratio of manganese:rhodium of (0.2 to 20):1.

In the carbonylation process of the present invention it has been unexpectedly found that the manganese stabilizer has a beneficial effect on the carbonylation process at a much lower concentration than is described in J. Molecular Catalysis, 39 (1987) 115–136. The beneficial effect on the carbonylation reaction of manganese in the process of the present invention has been found to occur at a low partial pressure of carbon monoxide of less than or equal to 7 bar partial pressure, which would be carbonylation rate limiting in the absence of the manganese stabilizer whereas iodide salts such as lithium iodide have been found not to increase the carbonylation rate under such conditions.

Also, in the process of the present invention, the presence of a manganese stabilizer in the liquid reaction composition stabilizer the rhodium catalyst when carbonylation product is separated from the rhodium catalyst and manganese in the liquid reaction composition during the product recovery step at a partial pressure of carbon monoxide less than that in the carbonylation reactor.

Thus, according to another embodiment of the present invention there is provided a process for the carbonylation of an alkyl alcohol and/or a reactive derivative thereof which process comprises the steps of (i) contacting, in a carbonylation reactor, said alcohol and/or a reactive derivative thereof with carbon monoxide in a liquid reaction composition comprising (a) a rhodium catalyst, (b) alkyl halide, and (c) at least a finite concentration of water; (ii) recovering said carbonylation product from said reaction composition at a partial pressure of carbon monoxide of less than or equal to 7 bar in the presence of a stabilizer for the rhodium catalyst comprising manganese, at a molar ratio of manganese:rhodium of (0.2 to 20):1; and (iii) recycling from step (ii), said rhodium catalyst and said manganese stabilizer to said carbonylation step (i).

Suitable alkyl alcohols comprise $C_1$ to $C_{10}$, preferably $C_1$ to $C_6$, more preferably $C_1$ to $C_4$ alkyl alcohols and yet more preferably methanol. Preferably, the alkyl alcohol is a primary or secondary alkyl alcohol. The product of the carbonylation of an alcohol having n carbon atoms and/or a derivative thereof is a carboxylic acid having n+1 carbon atoms and/or an ester of a carboxylic acid having n+1 carbon atoms and the alcohol having n carbon atoms. Thus the product of carbonylation of methanol and/or a derivative thereof is acetic acid and/or methyl acetate.

Suitable reactive derivatives of the alkyl alcohol include the corresponding alkyl ester of the alcohol and the corresponding carboxylic acid product, dialkyl ethers and alkyl halides, preferably iodides or bromides. Suitable reactive derivatives of methanol include methyl acetate, dimethyl ether and methyl iodide. A mixture of alkyl alcohol and reactive derivatives thereof may be used as reactants in the process of the present invention. Preferably, methanol and/or methyl acetate and/or dimethyl ether are used as reactants. At least some of the alkyl alcohol and/or reactive derivative thereof will be converted to, and hence present as, alkyl esters in the liquid reaction composition by reaction with carboxylic acid product or solvent. The concentration in the liquid reaction composition, of alkyl ester is suitably in the range 0.1 to 70% by weight, preferably 0.5 to 50% by weight, more preferably 0.5 to 35% by weight.

Water may be formed in situ in the liquid reaction composition, for example, by the esterification reaction between alkyl alcohol reactant and carboxylic acid product. Water may be introduced to the carbonylation reactor together with or separately from other components of the liquid reaction composition. Water may be separated from other components of reaction composition withdrawn from the reactor and may be recycled in controlled amounts to maintain the required concentration of water in the liquid reaction composition. Suitably, the concentration of water in the liquid reaction composition is in the range 0.1 to 15% by weight, preferably 1 to 15% by weight. Preferably, the concentration of water is maintained below 14%, more preferably below 11% and yet more preferably below 8% by weight.

The rhodium component of the catalyst in the liquid reaction composition may comprise any rhodium containing compound which is soluble in the liquid reaction composition. The rhodium component of the catalyst may be added to the liquid reaction composition for the carbonylation reaction in any suitable form which dissolves in the liquid reaction composition or is convertible to a soluble form. Examples of suitable rhodium-containing compounds which may be added to the liquid reaction composition include $[Rh(CO)_2Cl]_2$, $[Rh(CO)_2I]_2$, $[Rh(Cod)Cl]_2$, rhodium (III) chloride, rhodium (III) chloridetrihydrate, rhodium (III) bromide, rhodium (III) iodide, rhodium (III) acetate, rhodium dicarbonylacetylacetonate, $RhCl_3(PPh_3)_3$ and $RhCl(CO)(PPh_3)_2$.

Preferably, the rhodium catalyst concentration in the liquid reaction composition is in the range 50 to 5000 ppm by weight of rhodium, preferably 100 to 1500 ppm.

The manganese stabilizer may comprise any manganese-containing compound which is soluble in the liquid reaction composition. The stabilizer may be added to the liquid reaction composition for the carbonylation reaction in any suitable form which dissolves in the liquid reaction composition or is convertible to soluble form.

Examples of suitable manganese-containing compounds which may be used include $Mn_2(CO)_{10}$, manganese (II) acetate, manganese (III) acetate, manganese (II) bromide, manganese (II) bromide tetrahydrate, manganese (II) chloride, manganese (II) chloride hydrate, manganese (II) iodide, manganese (II) oxide, manganese (III) oxide, manganese (IV) oxide, $Mn(CO)_5Br$, $Mn(CO)_5I$.

It is believed that the manganese stabilizer is active for promotion of the carbonylation reaction when it comprises manganese in a low oxidation state such as Mn(O) and/or Mn(I). Thus, if the manganese is added to the reaction composition in a higher oxidation state, such as for example as Mn(II), it may not exhibit a promoting effect for the carbonylation reaction unless or until it is converted to a lower oxidation state, for example by contacting with a suitable reducing agent such as hydrogen.

The molar ratio of manganese stabiliser:rhodium catalyst is (0.2 to 20):1, preferably (0.5 to 10):1.

Suitable alkyl halides have alkyl moieties corresponding to the alkyl moiety of the alkyl alcohol reactant and are preferably $C_1$ to $C_{10}$, more preferably $C_1$ to $C_6$ and yet more preferably $C_1$ to $C_4$ alkyl halides. Preferably the alkyl halide is an iodide or bromide, more preferably an iodide. Preferably, the concentration of alkyl halide in the liquid reaction composition is in the range 1 to 30%, preferably 1 to 20%, more preferably 2 to 16% by weight.

An iodide salt may also be present in the liquid reaction composition as a catalyst stabilizer. Such an iodide salt can be any metal iodide, quaternary ammonium iodide or quaternary phosphonium iodide salt. Preferably, the metal iodide is an alkali iodide or alkaline earth metal iodide, more preferably an iodide of lithium, sodium, potassium or cesium. Suitable quaternary ammonium iodides include quaternized amine, pyridine, pyrrolidine or imidazole for example N,N' dimethyl imidazolium iodide. Suitable quaternary phosphonium iodides include methyl tributyl phosphonium iodide, tetrabutyl phosphonium iodide, methyl triphenyl phosphonium iodide and the like. Such iodide salt stabilisers are described, for example in EP-A-0573189.

The carbon monoxide reactant may be essentially pure or may contain inert impurities such as carbon dioxide, methane, nitrogen, noble gases, water and $C_1$ to $C_4$ paraffinic hydrocarbons. The presence of hydrogen in the carbon monoxide and generated in situ by the water gas shift reaction is preferably kept low, for example, less than 1 bar partial pressure, as its presence may result in the formation of hydrogenation products. The partial pressure of carbon monoxide in the reactor and/or product recovery steps is less than or equal to 7 bar, under which conditions it has been found that the use of a manganese stabilizer according to the process of the present invention in the reactor has a beneficial effect on the carbonylation reaction by stabilizing the catalyst and maintaining the rate of reaction.

The pressure of the carbonylation reaction is suitably in the range 10 to 200 barg, preferably 10 to 100 barg, more preferably 15 to 50 barg. The temperature of the carbonylation reaction is suitably in the range 100° to 300° C., preferably in the range 150° to 220° C., more preferably in the range 170° to 200° C.

Carboxylic acid and/or ester thereof may be used as a solvent for the reaction.

The process of the present invention may be performed as a batch or a continuous process, preferably as a continuous process.

The carboxylic acid and/or ester carbonylation product may be recovered from the liquid reaction composition by withdrawing liquid reaction composition from the reactor and separating the carbonylation product by one or more flash and/or fractional distillation stages from the other components of the liquid reaction composition such as rhodium catalyst, manganese stabilizer, alkyl halide, water and unconsumed reactants which may be recycled to the reactor to maintain their concentrations in the liquid reaction composition. The carbonylation product may also be removed as a vapour from the reactor.

In a preferred embodiment, liquid reaction composition comprising carboxylic acid product, rhodium catalyst, manganese stabiliser, alkyl halide, water, ester of the alkyl alcohol and the carboxylic acid product and unconsumed reactants is withdrawn from the reactor and passed to a flash separation zone at a total pressure less than of the carbonylation reactor, wherein with or without the addition of heat, vapour and liquid fractions are formed from the liquid reaction composition; the vapour fraction comprising carboxylic acid product, alkyl halide, water, unconsumed reactants and ester and the liquid fraction comprising carboxylic acid product, rhodium catalyst, manganese stabilizer, and water together with some alkyl halide and ester. The liquid fraction is recycled to the carbonylation reactor and the carboxylic acid product is recovered from the vapor fraction by one or more distillation stages, with the alkyl halide, water, ester and unconsumed reactants being recycled to the carbonylation reactor. The partial pressure of carbon monoxide in the flash separation zone is less than that in the carbonylation reactor, for example, less than 0.25 bar.

The invention will now be illustrated by way of example only by reference to the following examples.

In the Further Experiments described below manganese was found in the liquid reaction composition at the end of a batch carbonylation without the addition of manganese stabilizer at a concentration of about 6 ppm, due presumably, to corrosion. This corresponded to a molar ratio of manganese:rhodium of (significantly less than 0.05):1. It is therefore to be assumed that in the reported experiments without addition of manganese stabilizer, similar levels of manganese might be expected, that is a molar ratio of manganese:rhodium of (significantly less than 0.05):1.

The following experiments were performed using a 150 ml Hastelloy B2 (Trade Mark) autoclave equipped with a Magnedrive (Trade Mark) stirrer, liquid injection facility and cooling coils. A gas supply to the autoclave was provided from a ballast vessel, feed gas being provided to maintain the autoclave at a constant pressure. The rate of gas uptake at a certain point in a reaction run was used to calculate the carbonylation rate (with an accuracy believed to be +/−1%), as number of moles of reactant consumed per liter of cold degassed reactor composition per hour (mol/l/hr), at a particular reaction composition (reaction composition based on a cold degassed volume).

The methyl acetate concentration was calculated during the course of the reaction from the starting composition, assuming that one mole of methyl acetate is consumed for every mole of carbon monoxide that is consumed. No allowance was made for organic components in the autoclave headspace.

At the end of each experiment liquid and gas samples from the autoclave were analysed by gas chromatography.

For each batch carbonylation experiment the autoclave was charged with the manganese stabilizer (where applicable), the liquid components of the liquid reaction composition excluding part of the methyl acetate and/or acetic acid charge in which the rhodium catalyst was dissolved.

The autoclave was flushed twice with nitrogen and was then heated with stirring (1000 rpm) to 185° C. On attaining a temperature of 185° C. nitrogen was introduced into the autoclave to achieve a desired pressure, less than the final reaction pressure. The gas feed lines were then vented free of nitrogen and filled with carbon monoxide. After allowing the system to stabilize for about 30 minutes, the rhodium catalyst dissolved in methyl acetate and/or acetic acid was injected into the autoclave using an over pressure of carbon monoxide. The autoclave pressure was subsequently maintained at a constant pressure by feeding carbon monoxide gas on demand from the ballast vessel through the liquid injection facility, this pressure being between 27 and 28 barg. The initial partial pressure of carbon monoxide employed in the experiment was then calculated by subtracting the observed pressure when nitrogen was introduced to the autoclave from the final reactor pressure.

Gas uptake from the ballast vessel was measured every 30 seconds and from this was calculated the rate of carbonylation. After uptake of carbon monoxide from the ballast vessel has ceased or the reaction had proceeded for a period of 40 minutes, whichever was sooner, the autoclave was isolated from the gas supply. The autoclave was subsequently cooled to room temperature and the gases in the head space of the autoclave were cautiously vented from the autoclave, sampled and analyzed. The liquid reaction composition was discharged from the autoclave, sampled and analyzed for liquid products and by-products.

To obtain a reliable baseline a number of identical baseline runs may have to be performed to condition the autoclave such that consistent rates are achieved. This conditioning period is often different from autoclave to autoclave and may depend upon its previous history.

In the batch autoclave experiments and examples, the concentrations of components changed during the experiment as the reaction proceeded. Thus, the methyl acetate derivative of the methanol reactant decreased in concentration as did the water concentration. Methyl iodide promoter concentration decreased slightly as the volume of the liquid reaction composition increased due to formation of carboxylic acid product. The initial methyl acetate concentration (about 18% by weight) was higher than might be expected to be used in a typical continuous process (for example about 0.1 to 5% by weight) which concentration would occur in the batch experiment as methyl acetate conversion progressed to completion.

The autoclave charges, carbon monoxide partial pressures and reaction pressures for Experiments A–G and Examples 1–3 are shown in Table 1.

The results of the analyses of the non-condensable gases vented at the end of the experiments are given in Table 2. Analyses of the liquid reaction compositions showed that acetic acid is the major product (>99%) in all cases. All reactions were undertaken at 185° C.

Experiment A

A baseline experiment was performed at a relatively high water concentration ranging from 17.1 to 11.7% by weight during the course of the reaction. The initial partial pressure of carbon monoxide in the carbonylation reactor was 4.8 bar.

The reaction rate was calculated to be 3.6 mol/l/hr after 5 minutes, based upon uptake of carbon monoxide. The reaction ceased after only 104 mmol of carbon monoxide had been fed from the ballast vessel. This corresponded to the carbonylation of 43% of the methyl acetate substrate. On opening the autoclave evidence of extensive catalyst precipitation was found.

This is not an example according to the present invention because no manganese stabilizer was added to the liquid reaction composition. This experiment showed that at low partial pressure of carbon monoxide in the carbonylation reactor, the rate of reaction was only 3.6 mol/l/hr after five minutes under these conditions and that the reaction ceased, presumably because of deactivation and/or instability of the rhodium catalyst in the carbonylation reactor. The rate of reaction was lower than that which might be expected ( about 7.5 to 8 mol/l/hr) under similar conditions, but without the addition of nitrogen to the autoclave, that is at a partial pressure of carbon monoxide of greater than 7 bar.

The presence of a catalyst precipitate at the end of the experiment indicated that, in a process in which carboxylic acid product is separated at reduced carbon monoxide partial pressure from the rhodium catalyst in the reaction composition, the stability of the rhodium catalyst could be low.

Experiment B

A further baseline experiment was performed at a lower carbon monoxide partial pressures than that used in Experiment A.

The reaction rate was calculated to be 2.4 mol/l/hr after 5 minutes, based upon uptake of carbon monoxide. The reaction ceased after only 56 mmol of carbon monoxide had been fed from the ballast vessel. This corresponded to carbonylation of 23% of the methyl acetate substrate. On opening the autoclave there was evidence of significant catalyst precipitation.

This is not an example according to the present invention because no manganese stabilizer was added to the liquid reaction composition. This again indicated a low rate of reaction, early cessation of the reaction and the potential for catalyst instability during separation of carboxylic acid product from rhodium catalyst.

EXAMPLE 1

Experiment B was repeated except that $Mn_2(CO)_{10}$ (1.97 mmol) was also charged to the autoclave.

The carbonylation rate after 5 minutes was calculated to be 8.0 mol/l/hr. The rate of uptake of carbon monoxide (mol/hr) from the ballast vessel was constant until more than 90% of the methyl acetate had been consumed during the course of the reaction (based on carbon monoxide uptake). Furthermore, there was no evidence of catalyst precipitation on opening the autoclave at the end of the reaction.

This example is according to the present invention since it demonstrated that addition of manganese stabilizer $Mn_2(CO)_{10}$ to the carbonylation mixture at a low partial pressure of carbon monoxide increased the rate of carbonylation reaction and provided that the rate was maintained throughout the reaction implying increased stability of the rhodium catalyst in the reactor. Also, because conditions in the batch autoclave experiment were a more severe test of catalyst stability than those that might generally be expected during separation of carboxylic acid from the rhodium catalyst in the reaction composition (in particular the temperature and residence times are high), the lack of a precipitate indicated that the presence of the manganese stabilizer will stabilize the rhodium catalyst in a process where the carboxylic acid is separated from the rhodium catalyst in the reaction composition at a partial pressure of carbon monoxide less than that of the reactor.

EXAMPLE 2

Example 1 was repeated except that the reaction was performed at a constant pressure of 27.4 barg and an initial carbon monoxide partial pressure of 4.7 bar. The carbonylation rate after 5 minutes was calculated to be 7.5 mol/l/hr. The rate of uptake of carbon monoxide (mol/hr) from the ballast vessel was constant throughout the course of the reaction (run to completion based on uptake of carbon monoxide from the ballast vessel). Again, there was no evidence of catalyst precipitation on opening the autoclave at the end of the reaction.

This example is according to the present invention and further demonstrated that addition of manganese stabilizer $Mn_2(CO)_{10}$ to the carbonylation reaction composition afforded benefits of carbonylation rate promotion and catalyst stabilization and the benefit of catalyst stabilization during separation of the carboxylic acid product from the rhodium catalyst in the reaction composition.

Experiment C

An experiment was performed at a lower water concentration than employed in Experiments A and B ranging from 5.1 to 0.5% by weight during the course of the reaction. The reaction was performed at a constant pressure of 27.3 barg and at a initial partial pressure of carbon monoxide of 4.3 bar.

The reaction rate was calculated to be 0.9 mol/l/hr after 5 minutes, based upon uptake of carbon monoxide. The reaction ceased after only 14 mmol of carbon monoxide had been fed from the ballast vessel. This corresponded to carbonylation of 6% of the methyl acetate substrate. On opening the autoclave evidence of extensive catalyst precipitation was found.

This is not an example according to the present invention because no manganese stabilizer was added to the liquid reaction composition. This experiment indicated that a low rate of reaction, early cessation of the reaction and the potential for catalyst instability occurred when the concentration of water in the liquid reaction composition and the partial pressure of carbon monoxide were low.

Experiment D

Experiment C was repeated with the addition of lithium iodide (iodide salt stabilizer).

The reaction rate after 5 minutes was calculated to be 1.2 mol/l/hr which, within experimental error, is the same as in Experiment C. The reaction ceased after only 40 mmol of carbon monoxide had been consumed. This corresponded to carbonylation of 16% of the methyl acetate substrate. There was no evidence of catalyst precipitation an opening the autoclave at the end of the reaction.

This experiment is not an example according to the present invention since no manganese stabilizer was added to the liquid reaction composition. This experiment shows that, whilst lithium iodide stabilized the rhodium catalyst against precipitation, it did not provide the benefit of increasing the carbonylation rate under conditions of low partial pressure of carbon monoxide.

EXAMPLE 3

Experiment D was repeated except that manganese stabiliser $Mn_2(CO)_{10}$ (2.00 mmol) was added to the autoclave instead of the lithium iodide. The carbonylation rate after 5 minutes was calculated to be 4.9 mol/l/hr. The carbonylation rate decreased progressively during the course of the reaction and the reaction, which was still proceeding, was stopped after 40 minutes.

Some solid formation was observed at the end of the experiment, this was believed to be manganese salt rather than rhodium catalyst because it was different in character to typical rhodium precipitate observed in Experiments A and B.

This example is according to the present invention. It demonstrated that addition of manganese stabilizer $Mn_2(CO)_{10}$ to the carbonylation mixture at a low partial pressure of carbon monoxide increased the rate of carbonylation reaction.

Also, as previously discussed, lack of a rhodium catalyst precipitate indicated that the presence of the manganese stabilizer will stabilize the rhodium catalyst in a process where the carboxylic acid is separated from the rhodium catalyst at a partial pressure of carbon monoxide less than that in the reactor.

Furthermore, the example showed that manganese was superior to equimolar concentrations of LiI at low partial pressures of carbon monoxide.

Experiment E

A baseline experiment was performed at a low water concentration (ranging from 5.1 to 0.5 wt %) as in Experiment C. However, no nitrogen was added to the autoclave prior to introduction of carbon monoxide so the partial pressure of carbon monoxide, though not calculated, was greater than 7 bar. The carbonylation rate after 5 minutes was 6.9 mol/l/hr. The carbonylation rate was not constant during the reaction, and decreased progressively until the reaction was stopped after 40 minutes. This indicated a progressive deactivation of the rhodium catalyst as the water concentration decreased during the experiment.

This is not an example according to the present invention because no manganese stabilizer was added to the liquid reaction composition.

Experiment F

Experiment E was repeated except that lithium iodide (3.81 mmol) was added to the reaction composition. The carbonylation rate was not constant during the reaction, but decreased progressively from an initial rate of 6.8 mol/l/hr, measured after 5 minutes, until the reaction was stopped after 40 minutes.

This is not an example according to the present invention because no manganese stabilizer was added to the liquid reaction composition. This experiment demonstrated that addition of lithium iodide (a known carbonylation catalyst stabilizer) to the liquid reaction composition, did not overcome the disadvantage of decreasing rate of carbonylation (and hence catalyst activity) during the course of this experiment. Neither was the rate of carbonylation reaction after 5 minutes increased.

Experiment G

Experiment E was repeated except that $Mn_2(CO)_{10}$ (1.95 mmol) was also charged to the autoclave.

The carbonylation rate during the reaction was not constant, but decreased progressively from an initial rate of 6.8 mol/l/hr, measured after 5 minutes, until the reaction was stopped after 40 minutes.

This is not an example according to the present invention because the partial pressure of carbon monoxide was greater than 7 bar. The experiment showed that under these conditions, manganese did not promote the carbonylation reaction.

TABLE 2-continued

| | Analyses of non-condensable gases | |
|---|---|---|
| | $CH_4$ (% v/v) | $CO_2$ (% v/v) |
| Experiment F | — | trace |
| Experiment G | 4.0 | 0.8 | a. balance comprising hydrogen (not measured), nitrogen and carbon monoxide

TABLE 1

Autoclave Charge and Carbonylation Rate After 5 Minutes

| Experiment/ Example | Methyl acetate (mmol) | Water (mmol) | Methyl iodide (mmol) | Acetic acid (mmol) | Mn dimer (d) (mmol) | Rh dimer (d) (mmol) | Lithium iodide (mmol) | Reactor Pressure (barg) | Initial CO Partial Pressure (bar) | Carbonylation rate after 5 minutes (mol/l/hr) |
|---|---|---|---|---|---|---|---|---|---|---|
| Experiment A | 244 | 911 | 101 | 704 | — | 0.20 (a) | — | 27.5 | 4.8 | 3.6 |
| Experiment B | 244 | 911 | 102 | 703 | — | 0.20 (a) | — | 27.3 | 4.3 | 2.4 |
| Example 1 | 237 | 910 | 101 | 711 | 1.97 | 0.20 (b) | — | 27.0 | 4.1 | 8.0 |
| Example 2 | 237 | 910 | 101 | 711 | 1.97 | 0.20 (b) | — | 27.4 | 4.7 | 7.5 |
| Experiment C | 237 | 273 | 101 | 905 | — | 0.20 (b) | — | 27.3 | 4.3 | 0.9 |
| Experiment D | 238 | 272 | 101 | 903 | — | 0.20 (b) | 3.81 | 27.2 | 4.1 | 1.2 |
| Example 3 | 237 | 272 | 101 | 903 | 2.00 | 0.20 (b) | — | 27.3 | 4.3 | 4.9 |
| Experiment E | 244 | 272 | 99 | 894 | — | 0.20 (a) | — | 27.0 | (c) | 6.9 |
| Experiment F | 244 | 271 | 99 | 894 | — | 0.20 (a) | 3.81 | 27.0 | (c) | 6.8 |
| Experiment G | 237 | 273 | 101 | 903 | 1.95 | 0.20 (b) | — | 27.1 | (c) | 6.8 |

(a) Dissolved in 83 mmol of acetic acid.
(b) Dissolved in 75 mmol of acetic acid and 7 mmol of methyl acetate.
(c) Not calculated.
(d) Mn dimer: $Mn_2(CO)_{10}$ Rh dimer: $Rh_2Cl_2(CO)_4$.

TABLE 2

| | Analyses of non-condensable gases | |
|---|---|---|
| | $CH_4$ (% v/v) | $CO_2$ (% v/v) |
| Experiment A | 9.8 | 4.4 |
| Experiment B | 9.5 | 3.8 |
| Example 1 | 5.1 | 2.3 |
| Example 2 | 8.5 | 7.7 |
| Experiment C | 0.4 | 0.5 |
| Experiment D | 2.4 | 0.7 |
| Example 3 | 4.7 | 1.0 |
| Experiment E | — | trace |

Further Experiments

Experiments were performed in an analogous manner to those described in Experiments A–G and Examples 1–3, using a 300 ml Hastelloy B2 (Trade Mark). Gas uptake from the ballast vessel was measured every 2 seconds (rather than every 30 seconds as described previously) and from this was calculated the rate of carbonylation. Reactions were performed at constant pressures of between 26 and 28 barG.

The autoclave charges are given in Table 3 below.

TABLE 3

Autoclave Charges

| Experiment/ Example | Methyl acetate (mmol) | Water (mmol) | Methyl iodide (mmol) | Acetic acid (mmol) | Mn (mmol) | Rh [1] (mmol) | Lithium iodide (mmol) |
|---|---|---|---|---|---|---|---|
| Experiment H | 474 | 545 | 203 | 1507 | — | 0.40 | 150 |
| Experiment I | 477 | 540 | 204 | 1506 | — | 0.40 | 149 |
| Example 4 | 475 | 547 | 203 | 1482 | 3.90 [2] | 0.40 | 149 |
| Example 5(a) | 475 | 547 | 203 | 1465 | 7.84 [3] | 0.40 | 150 |
| Example 5(b) | 476 | 546 | 206 | 1469 | 7.74 [3] | 0.40 | 149 |

[1] $Rh_2(CO)_4Cl_2$ dissolved in 117 mmol acetic acid and 13 mmol methyl acetate.
[2] $Mn_2(CO)_{10}$
[3] $MnI_2$

Experiment H

An experiment was performed in which lithium iodide was present in the liquid reaction composition at an initial concentration 10.4% by weight. The water concentration in the liquid reaction composition ranged from 5.1% to 0.5% by weight during the course of the reaction. The reaction was performed at a constant pressure of 28.2 barG and at an initial carbon monoxide partial pressure of 5.5 bar.

The reaction rate was calculated to be 2.6 mol/l/hr at a water concentration of 4.5% by weight. The reaction was stopped after only 11 mmol of carbon monoxide had been feed from the ballast vessel.

This is not an example according to the present invention because no manganese was added to the liquid reaction composition. This experiment showed that, even in the presence of a high concentration of lithium iodide, a poor reaction rate was obtained at a low carbon monoxide partial pressure.

Experiment I

Experiment H was repeated except that hydrogen (1 bar) was introduced to the autoclave prior to warming to 185° C. The reaction was performed at an initial constant pressure of 26.1 barG and with an initial carbon monoxide partial pressure of 5.3 bar.

The reaction rate was calculated to be 3.5 mol/l/hr measured at a water concentration of 4.5% by weight. The reaction was stopped after 320 mmol of carbon monoxide had been consumed from the ballast vessel.

Experiment I is not according to the present invention but demonstrated that hydrogen had some limited beneficial effect on reaction rate at the low carbon monoxide partial pressure.

EXAMPLE 4

Experiment H was repeated with the addition of $Mn_2(CO)_{10}$ (3.90 mmol). The autoclave pressure was 27 barG and the initial partial pressure of carbon monoxide was 4.7 bar.

The reaction ran until completion. At a water concentration of 4.5% by weight, the carbonylation rate was be 8.0 mol/l/hr.

Example 4 is according to the present invention. It demonstrated that the addition of the manganese stabilizer $Mn_2(CO)_{10}$ enhanced the carbonylation rate at low carbon monoxide pressure in the presence of lithium iodide. Also, it showed that this manganese stabilizer was superior to the beneficial effect of hydrogen (1 bar measured at ambient conditions) in promoting this carbonylation reaction.

EXAMPLE 5

EXAMPLE 5(a)

Example 4 was repeated except that $MnI_2$ (7.84 mmol) was used as the manganese stabilizer. The reactor pressure was 28.5 barG and the partial pressure of carbon monoxide was initially 6.0 bar.

The reaction rate measured at a water concentration of 4.5% by weight was 2.0 mol/l/hr.

This experiment shows that this manganese (II) stabiliser was not effective in promoting the carbonylation reaction during the period of this batch autoclave reaction.

EXAMPLE 5(b)

Example 5(a) was repeated except that hydrogen (1 bar) was introduced to the autoclave prior to warming to reaction temperature. The reactor pressure was 26.5 barG and the initial partial pressure of carbon monoxide was calculated to be 5.1 bar.

The reaction rate was 4.2 mol/l/hr measured at a water concentration of 4.5% by weight.

This example is according to the present invention as it showed that hydrogen could be used to activate the manganese (II) stabilizer at the low carbon monoxide partial pressure. Furthermore, the reaction rate was superior to that which was observed in Experiment I.

I claim:

1. A process for the carbonylation of an alkyl alcohol and/or a reactive derivative thereof which process comprises the steps of (i) contacting, in a carbonylation reactor, said alcohol and/or a reactive derivative thereof with carbon monoxide in a liquid reaction composition comprising (a) a rhodium catalyst, (b) alkyl halide, and (c) at least a finite concentration of water and (ii) recovering carbonylation product from said liquid reaction composition characterized in that there is present in the carbonylation and/or product recovery steps a partial pressure of carbon monoxide less than or equal to 7 bar and a stabilizer for the rhodium catalyst comprising manganese, at a molar ratio of manganese:rhodium of(0.2 to 20):1.

2. A process as claimed in claim 1 in which the molar ratio of manganese:rhodium is (0.5 to 10 ):1.

3. A process as claimed in claim 1 which comprises contacting, in a carbonylation reactor, an alcohol and/or a reactive derivative thereof with carbon monoxide in a liquid reaction composition at a partial pressure of carbon monoxide in said reactor of less than or equal to 7 bar, in which the liquid reaction composition comprises (a) a rhodium catalyst, (b) alkyl halide, (c) at least a finite concentration of water and (d) a stabilizer for the rhodium catalyst comprising manganese in a form active for promotion of the carbonylation reaction at a molar ratio of manganese:rhodium of (0.2 to 20):1.

4. A process as claimed in claim 3 in which the manganese stabilizer is present in the liquid reaction composition as manganese (I).

5. A process as claimed in claim 4 in which the liquid reaction composition comprises water at a concentration below 14% by weight.

6. A process as claimed in claim 5 in which the liquid reaction composition further comprises an iodide salt stabilizer selected from the group consisting of metal iodides, quaternary ammonium iodides and quaternary phosphonium iodides.

7. A process as claimed in claim 6 in which the metal iodide salt stabilizer is selected from the group consisting of alkali iodides and alkaline earth metal iodides; the quaternary ammonium iodide is selected from the group consisting of quaternary amines, pyridines, pyrrolidines and imidazoles; and the quaternary phosphonium iodide is selected from the group consisting of methyl tributyl phosphonium iodide, tetrabutyl phosphonium iodide and methyl triphenyl phosphonium iodide.

8. A process as claimed in claim 3 in which the manganese stabilizer is converted to an active form by contacting with hydrogen.

9. A process as claimed in claim 3 in which the molar ratio of manganese:rhodium in the liquid reaction composition is (0.5 to 10):1.

10. A process as claimed in claim 1 which comprises contacting, in a carbonylation reactor, methanol and/or methyl acetate with carbon monoxide in a liquid reaction composition at a partial pressure of carbon monoxide in said reactor of less than or equal to 7 bar and in which the liquid reaction composition comprises (a) a rhodium catalyst at a concentration in the liquid reaction composition of 100 to 1500 ppm by weight of rhodium, (b) 2 to 16% by weight methyl iodide, (c) less than 8% by weight water, and (d) a stabilizer for the rhodium catalyst comprising manganese in a form active for promotion of the carbonylation reaction at a molar ratio of manganese stabilizer:rhodium catalyst of (0.5 to 10):1.

11. A process as claimed in claim 1 which comprises the steps of (i) contacting, in a carbonylation reactor, said alcohol and/or a reactive derivative thereof with carbon monoxide in a liquid reaction composition comprising (a) a rhodium catalyst, (b) alkyl halide, and (c) at least a finite concentration of water; (ii) recovering said carbonylation product from said reaction composition at a partial pressure of carbon monoxide of less than or equal to 7 bar in the presence of a stabilizer for the rhodium catalyst comprising manganese, at a molar ratio of manganese:rhodium of (0.2 to 20):1; and (iii) recycling from step (ii), said rhodium catalyst and said manganese stabilizer to said carbonylation step (i).

12. A process as claimed in claim 11 in which the partial pressure of carbon monoxide in step (ii) is less than 0.25 bar.

13. A process as claimed in claim 12 in which the alkyl alcohol comprises methanol and the carbonylation product comprises acetic acid.

14. A process as claimed in claim 13 in which the molar ratio of manganese:rhodium in step (ii) is (0.5 to 10):1.

15. A process as claimed in claim 4 in which the molar ratio of manganese:rhodium in the liquid reaction composition is (0.5 to 10):1.

16. A process as claimed in claim 5 in which the molar ratio of manganese:rhodium in the liquid reaction composition is (0.5 to 10):1.

17. A process as claimed in claim 6 in which the molar ratio of manganese:rhodium in the liquid reaction composition is (0.5 to 10):1.

18. A process as claimed in claim 7 in which the molar ratio of manganese:rhodium in the liquid reaction composition is (0.5 to 10):1.

19. A process as claimed in claim 8 in which the molar ratio of manganese:rhodium in the liquid reaction composition is (0.5 to 10):1.

20. A process as claimed in claim 5 in which the liquid reaction composition comprises water at a concentration below 11% by weight.

21. A process as claimed in claim 20 in which the liquid reaction composition comprises water at a concentration below 8% by weight.

22. A process as claimed in claim 7 in which the metal iodide salt stabilizer is selected from the group consisting of iodides of lithium, sodium, potassium and cesium.

23. A process as claimed in claim 7 in which the quaternary ammonium iodide is N,N' dimethyl imidazolium iodide.

* * * * *